United States Patent [19]

Boyle et al.

[11] Patent Number: 4,789,677
[45] Date of Patent: Dec. 6, 1988

[54] N-ALKYL-[N-[N-ALKYL-N-[4-(4-QUINOLINYLAMINO)BENZOYL-]AMINO]ALKYL]BENZENESULPHONAMIDES

[75] Inventors: John T. A. Boyle, Cookham; Richard S. Todd, Burnham, Nr. Slough, both of England

[73] Assignee: John Wyeth and Brothers Limited, Maidenhead, England

[21] Appl. No.: 94,063

[22] Filed: Sep. 2, 1987

Related U.S. Application Data

[63] Continuation of Ser. No. 831,220, Feb. 20, 1986, abandoned.

[30] Foreign Application Priority Data

Mar. 2, 1985 [GB] United Kingdom ............. 8505430

[51] Int. Cl.⁴ .................. C07D 215/44; A61K 31/47
[52] U.S. Cl. .................................. 514/313; 546/161; 564/94

[56] References Cited

U.S. PATENT DOCUMENTS

| | | | |
|---|---|---|---|
| 3,632,761 | 1/1972 | Graham et al. | 546/161 |
| 4,025,629 | 5/1977 | Coverdale | 546/161 |
| 4,167,567 | 9/1979 | McCall | 544/212 |
| 4,235,908 | 11/1980 | Boyle | 514/313 |
| 4,640,920 | 2/1987 | Boyle | 544/235 |

FOREIGN PATENT DOCUMENTS

| | | |
|---|---|---|
| 2039233 | 2/1971 | Fed. Rep. of Germany . |
| 124758 | 7/1983 | Japan . |
| 2021567 | 5/1978 | United Kingdom . |
| 2159815 | 12/1985 | United Kingdom ........ 564/92 |

OTHER PUBLICATIONS

Chemical Abstracts for DE 2,039,233 (2/18/71) 74:99900f (1971), Graham et al.

Chemical Abstracts for JP 124758 (7/25/83), 100:34278v (1984), Fujisawa Pharmaceutical.

Wendling et al., Fed. Proc., 42, 162–166 (1983).

*Primary Examiner*—Donald G. Daus
*Assistant Examiner*—E. Bernhardt
*Attorney, Agent, or Firm*—Arthur G. Seifert

[57] ABSTRACT

New compounds having the formula I

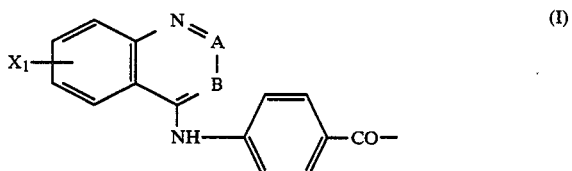

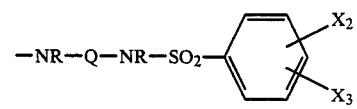

where one of A and B is CH or N, the other of A and B is CH, Q is lower alkylene, R is lower alkyl, $X_1$ is halogen or trifluoromethyl and $X_2$ and $X_3$ are independently selected from hydrogen, halogen, trifluoromethyl, lower alkoxy and lower alkyl and the pharmaceutically acceptable acid additions are disclosed as anti-hypertensive agents. New compounds having the formula II

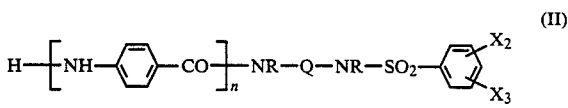

where Q, R, $X_2$ and $X_3$ are as explained above and n is 0 or 1 and their acid addition salts are useful as intermediates.

6 Claims, No Drawings

N-ALKYL-[N-[N-ALKYL-N-[4-(4-QUINOLINYLAMINO)BENZOYL]AMINO]ALKYL]BENZENESULPHONAMIDES

This application is a continuation of application Ser. No. 831,220, filed Feb. 20, 1986, now abandoned.

The invention relates to novel benzamide derivatives that are useful as pharmaceuticals, particularly as antihypertensive agents, processes for their preparation and pharmaceutical compositions containing them. The invention also relates to intermediates for their preparation.

1-[(4-fluorophenyl)sulphonyl]-4-[4-[(7-trifluoromethyl)-4-quinolyl)amino]benzoyl]piperazine is one of a class of compounds having antihypertensive activity disclosed in GB 2,021,567A. Pharmacological studies of this compound are reported in Federation Proceedings, 42, 162-166 (1983). The inventors have investigated the replacement of the piperazine component of the known compound by some open chain bifunctional amines. It has been surprisingly found that the replacement may increase the antihypertensive effect as is shown in Table 1 below.

The invention provides a new compound having the formula I

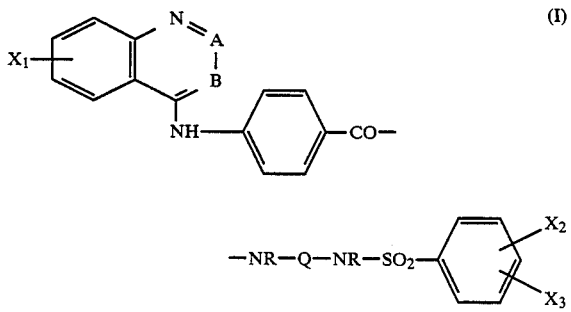

or a pharmaceutically acceptable acid addition salt thereof, wherein either one of A and B is selected from CH and N whilst the other of A and B is CH; Q is lower alkylene; R is lower alkyl; $X_1$ is halogen or trifluoromethyl and $X_2$ and $X_3$ are independently selected from hydrogen, halogen, trifluoromethyl, lower alkyl and lower alkoxy. These compounds are particularly indicated for use as pharmaceuticals, particularly as antihypertensive agents.

When both of A and B are CH, the end compounds of the invention are quinoline derivatives. When A is CH whilst B is N the end compounds are quinazoline derivatives. Where A is N whilst B is CH the end compounds are cinnoline derivatives. Advantageously both A and B are CH. The substituent $X_1$ may be present at any one of the 5, 6, 7 and 8- positions of the quinoline, quinazoline or cinnoline ring system, but is preferably at the 7- or 8- position, advantageously at the 7- position. The substituent $X_1$ is halogen, for instance, chlorine or bromine, or trifluoromethyl. $X_1$ is preferably trifluoromethyl.

The group Q represents lower alkylene. The lower alkylene group may be branched or in the form of a straight chain. As examples there may be mentioned methylene, dimethylene, trimethylene or tetramethylene. The lower alkylene group is preferably in the form of a straight chain and is advantageously dimethylene, i.e. a group having the formula —$(CH_2)_2$—.

The substituent R is lower alkyl. As examples methyl, ethyl, propyl or butyl may be mentioned. Methyl is preferred.

$X_2$ and $X_3$ independently represent hydrogen, halogen (for instance, fluorine, chlorine or bromine), trifluoromethyl, lower alkyl (for instance methyl, ethyl, propyl or butyl) or lower alkoxy (for instance methoxy, ethoxy, propoxy or butoxy). $X_2$ and $X_3$ together with the phenyl group to which they are attached preferably represent mono (halo or trifluoromethyl) phenyl, advantageously p-fluorophenyl.

The term "lower" as used herein to refer to such groups as alkylene, alkyl and alkoxy indicates that the group contains up to 6, preferably up to 4, carbon atoms.

The compounds having formula I form acid addition salts with acids. Examples of such salts are those formed from inorganic and organic acids and in particular include the sulphate, hydrochloride, hydrobromide, hydroiodide, nitrate, phosphate, sulphonates (for instance the methanesulphonate or p-toluenesulphonate), acetate, maleate, fumarate, tartrate, malonate, citrate or formate.

The invention also provides, as novel intermediates, compounds having the formula II

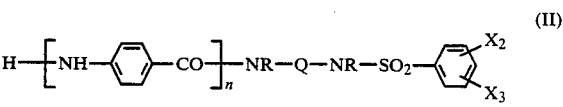

(wherein Q, R, $X_2$ and $X_3$ are as defined above and n is 0 or 1) and their acid addition salts.

The compounds having formula I and their pharmaceutically acceptable salts are preferably prepared by a process in which (a) a compound having formula II (in which n is 0 and Q, R, $X_2$ and $X_3$ are as defined above) or a salt thereof is reacted with a compound having the formula (III)

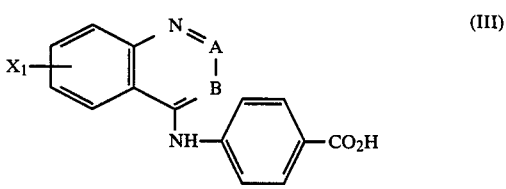

(wherein A, B and $X_1$ are as defined above) or a reactive derivative thereof; or (b) a compound having formula II (in which n is 1 and Q, R, $X_1$ and $X_2$ are as defined above) or a salt thereof is reacted with a compound having the formula IV

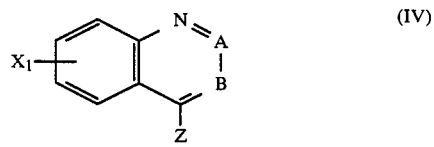

(wherein $X_1$, A and B are as defined above and Z is a leaving group or atom preferably a halogen atom such as chlorine, bromine or iodine); or (c) a compound having the formula

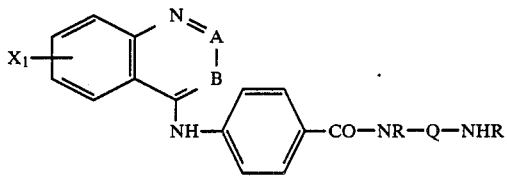

(wherein $X_1$, A, B, Q and R are as defined above) or a salt thereof is sulphonylated to introduce the sulphonyl group having the formula VI

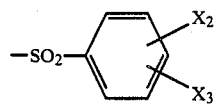

(wherein $X_2$ and $X_3$ are as defined above). If desired the process may also include the step of converting a free base form of the compound having formula I into a pharmaceutically acceptable acid addition salt thereof by addition of an acid or conversion of an acid addition salt form of a compound having formula I into the free base form of the compound having formula I, for instance, by neutralisation with a base.

Process step (a) may be carried out in known manner for the acylation of amines. The amine having formula II in which n is 0 may be reacted with the acid having formula III in the presence of a condensing agent, for instance, a carbodiimide. Alternatively the amine may be reacted with a reactive derivative of the acid as acylating agent, for instance, an active ester, simple or mixed anhydride, an acyl halide, preferably the acyl chloride, or the acid azide.

The acids having formula III are known in the art or may be prepared in known manner, for instance, by reacting p-aminobenzoic acid with a compound having formula IV. The preparation of the amines of formula II where n is 0 is described below.

Process step (b) may be carried out in aqueous alcohol with or without acid catalysts. The compounds having formula IV are generally known or, where new, can be prepared in known manner. The preparation of the amines having formula II where n is 1 is described below.

Process step (c) may be carried out by using a sulphonyl chloride having the formula $X_4$-Cl (where $X_4$ is the sulphonyl group of formula VI) as sulphonylating agent. The reaction can be carried out in known manner for the sulphonylation of amines. The sulphonylation may be carried out in a suitable solvent, for instance, chloroform or methylene chloride, in the presence of a base to neutralise the hydrogen chloride formed. The base may be provided by using, for instance, an alkali metal carbonate or bicarbonate or a tertiary amine, for instance, triethylamine or an excess of the basic compound having formula V. The sulphonyl chloride of formula $X_4$-Cl can be prepared from the corresponding sulphonic acid having formula $X_4$-OH by the use of thionyl chloride and dimethylformamide.

The compounds having formula V may be prepared by reacting an amine having the formula HNR-Q-NRX$_5$ (VII) (wherein Q and R are as defined above and $X_5$ is a suitable protecting group, for instance benzyl) with an acid having formula III or a reactive derivative thereof to form an amide and removing the protecting group $X_5$ from the resulting amide in known manner, for instance, by hydrogenolysis of a benzyl group as protecting group $X_5$.

The compounds having formula II where n is 0 and acid addition salts thereof may be prepared by a process in which a compound having the formula VIII

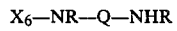

(where Q and R are as defined above and $X_6$ is hydrogen or a protecting group) or a salt thereof is mono-sulphonylated to introduce the sulphonyl group having formula VI (where $X_2$ and $X_3$ are as defined above) and if necessary the protecting group is removed. If desired, the process may include conversion of the free base form of the compound having formula II into an acid addition salt thereof by addition of an acid or conversion of an acid addition salt form of the compound having formula II into the free base form of the compound, for instance, by neutralisation with a base.

The sulphonylation reaction may be carried out in a similar manner to process step (c) as described above. The starting amine having formula VIII where $X_6$ is hydrogen contains two nitrogen atoms at which sulphonylation can take place. One method of avoiding disulphonylation is to use a starting compound having formula VIII where $X_6$ is a suitable protecting group, for instance, a benzyl group which can be removed by hydrogenolysis after the sulphonylation reaction. Alternatively monosulphonylation may be carried out by using the reactant of formula VIII where $X_6$ is hydrogen in a large stoichiometric excess.

The compounds having the formula II where n is 1 and their acid addition salts may be prepared by a process in which a compound having the formula II where n is 0 or a salt thereof is reacted with p-nitrobenzoic acid or a reactive derivative thereof to form an amide and the amide is reduced to convert the nitro group into amino. If desired the process may also include conversion of a free base form of the product of formula II where n is 1 into an acid addition salt or conversion of such an acid addition salt into the free base.

The p-nitrobenzoylation reaction may be carried out in known manner for the conversion of amines into amides. The reduction of the p-nitrobenzamide product to form the p-aminobenzamide compound having formula II in which n is 1 may be carried out by catalytic hydrogenation.

The novel compounds having general formula I and their pharmaceutically acceptable salts are indicated for use as anti-hypertensive agents. The compounds may be tested for their response on the blood pressure of spontaneously hypertensive rats in the following procedure:

The blood pressure of male or female conscious rats that are spontaneously hypertensive are measured in a 39° C. constant temperature housing by means of a tail cuff. Rats with systolic pressures below 155 mm Hg are not used. Groups of rats (4 per group) are dosed orally with the test substance in a suitable vehicle or with vehicle alone. Systolic pressures are recorded before dosing and at selected time points afterwards (2 hours and 6 hours).

Two compounds having formula IX

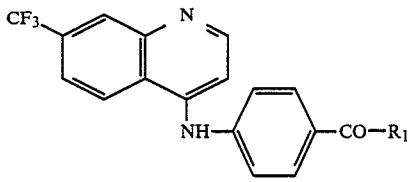

(IX)

where $R_1$ is as explained below were tested in the above procedure at a dose of 0.03 millimoles/kg p.o. and the results are presented in Table 1 below.

TABLE 1

| Compound Tested | | Blood Pressure (as % of initial value) | |
|---|---|---|---|
| Identification No. | Meaning of $R_1$ | After 2 hours | After 6 hours |
| 1 | $-N\begin{pmatrix}CH_2-CH_2\\CH_2-CH_2\end{pmatrix}N-SO_2-\text{C}_6\text{H}_4-F$ | 72 | 68 |
| 2 | $-N(CH_3)-CH_2-CH_2-N(CH_3)-SO_2-\text{C}_6\text{H}_4-F$ | 61 | 60 |

Compound 1 is the known compound referred to above. It was used in the form of the hydrochloride ⅓ ethanolate. Compound number 1 caused a 28% decrease in blood pressure after 2 hours and a 32% decrease after 6 hours. The compound was clearly active. Compound number 2 caused a 39% decrease in blood pressure after 2 hours and a 40% decrease after 6 hours and was therefore the more active of the two compounds tested. This result was surprising especially because there was no reason for expecting good activity in a compound derived from an open chain bifunctional amine.

The invention also provides a pharmaceutical composition comprising a compound having formula I or a pharmaceutically acceptable acid addition salt thereof in association with a pharmaceutically acceptable carrier. Any suitable carrier known in the art can be used to prepare the pharmaceutical composition. In such a composition, the carrier is generally a solid or liquid or a mixture of a solid and a liquid.

Solid form compositions include powders, granules, tablets, capsules (e.g. hard and soft gelatin capsules), suppositories and pessaries. A solid carrier can be, for example, one or more substances which may also act as flavouring agents, lubricants, solubilisers, suspending agents, fillers, glidants, compression aides, binders or tablet-disintegrating agents; it can also be an encapsulating material. In powders the carrier is a finely divided solid which is in admixture with the finely divided active ingredient. In tablets the active ingredient is mixed with a carrier having the necessary compression properties in suitable proportions and compacted in the shape and size desired. The powders and tablets preferably contain up to 99%, e.g. from 0.03 to 99%, preferably 1 to 80% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

The term "composition" is intended to include the formulation of an active ingredient with encapsulating material as carrier to give a capsule in which the active ingredient (with or without other carriers) is surrounded by the carrier, which is thus in association with it. Similarly cachets are included.

Liquid form compositions include, for example, solutions, suspensions, emulsions, syrups, elixirs and pressurised compositions. The active ingredient, for example, can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavouring agents, suspending agents, thickening agents, colours, viscosity regulators, stabilisers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycerol and glycols) and their derivatives and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilised by, for example, intramuscular, intraperitoneal or subcutaneous injection. Sterile solutions can also be administered intravenously. When the compound is orally active it can be administered orally either in liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule of any such compositions in package form. The quantity of the active ingredient in unit dose of composition may be varied or adjusted from 0.5 mg or less to 750 mg or more, according to the particular need and the activity of the active ingredient. The invention also includes the compounds in the absence of the carrier where the compounds are in unit dosage form.

The invention is illustrated by the following Example:

EXAMPLE

4-Fluoro-N-methyl-N-[2-[N-methyl-N-[4-(7-tri-fluoromethyl-4-quinolinylamino)benzoyl]amino]ethyl]-benzenesulphonamide (a)

4-Fluoro-N-methyl-N-[2-(methylamino)ethyl]benzene-sulphonamide

A solution of 4-fluorobenzenesulphonyl chloride (6.0 g) in chloroform (30 ml) was added dropwise to a well-stirred solution of N,N'-dimethyl-ethylenediamine (25 g) in chloroform (300 ml) at room temperature. After 2 hours the chloroform solution was vigorously shaken with aqueous sodium carbonate solution, separated, dried (MgSO₄) and evaporated under reduced pressure to give an oil. The oil was treated with chloroform (60 ml) and water (100 ml). The two solvents were mixed thoroughly and were then separated. The chloroform layer was dried (MgSO₄) and evaporated under reduced pressure to give an oil. Final traces of N,N'-dimethyl-ethylenediamine were removed by heating the oil under low vacuum to give 4-fluoro-N-methyl-N-[2-(methylamino)ethyl]benzenesulphonamide.

(b)

4-Fluoro-N-methyl-N-[2-[N-methyl-N-[4-(7-tri-fluoromethyl-4-quinolinylamino)benzoyl]amino]ethyl]-benzenesulphonamide 4-(7-Trifluoromethyl-4-quinolinylamino)benzoyl chloride hydrochloride (2.0 g) was added portionwise to a well-stirred mixture of sodium carbonate (8.0 g) and 4-fluoro-N-methyl-N-[2-(methylamino)ethyl]ben-zenesulphonamide (1.48 g) in chloroform (60 ml) and water (70 ml) at about 10° C. The mixture was warmed to room temperature and, after 1 hour, the chloroform layer was separated, dried (MgSO₄) and evaporated under reduced pressure to give an oil, which crystallised on standing. Recrystallisation from ethanol/water gave a white solid, which was further purified by recrystallisation from ethanol, giving the pure title compound (1.4 g), m.p. 191°–3° C.

Analysis: Found: C, 58.1%; H, 4.41%; N, 10.3%. $C_{27}H_{24}F_4N_4O_2S$ requires: C, 57.9%; H, 4.32%; N, 10.0%.

We claim:

1. A compound selected from those having the formula I

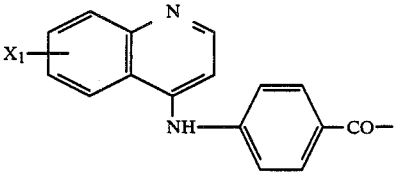

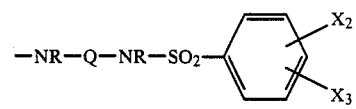

and their pharmaceutically acceptable acid addition salts, wherein Q is a straight or branched alkyl group of 1 to 6 carbon atoms; R is an alkyl group of 1 to 6 carbon atoms; $X_1$ is selected from halogen and trifluormethyl; and $X_2$ and $X_3$ are independently selected from hydrogen, halogen, trifluoromethyl, alkyl of 1 to 6 carbon atoms and alkoxy of 1 to 6 carbon atoms.

2. A compound as claimed in claim 1, wherein $X_1$ is at the 7- or 8-position of the quinoline ring system.

3. A compound of claim 1 wherein Q is a straight or branched alkyl group of 1 to 4 carbon atoms.

4. A compound of claim 1 wherein $X_2$ and $X_3$ are independently selected from halogen, trifluoromethyl, lower alkyl of 1 to 4 carbon atoms and lower alkoxy of 1 to 4 carbon atoms.

5. A compound as claimed in claim 1, wherein the compound having formula I is 4-fluoro-N-methyl-N-[2-[N-methyl-N-[4-(7-trifluoromethyl-4-quinolinylamino)-benzoyl]amino]ethyl]benzenesulphonamide.

6. A pharmaceutical composition useful as an anti-hypertensive agent comprising an anti-hypertensively effective amount of a compound as claimed in claim 1 in combination or association with a pharmaceutically acceptable carrier.

* * * * *